(12) United States Patent
Fursov et al.

(10) Patent No.: US 6,693,230 B1
(45) Date of Patent: Feb. 17, 2004

(54) SELF-DEFOLIATING PLANT

(75) Inventors: Viktor Fursov, Astrakhan (RU); Kamila Hulman, Vienna (AT)

(73) Assignee: Virgin Cotton Company, Stanmore (AU)

( * ) Notice: Subject to any disclaimer, the term of this patent is extended or adjusted under 35 U.S.C. 154(b) by 0 days.

(21) Appl. No.: 09/463,081

(22) PCT Filed: Jul. 20, 1998

(86) PCT No.: PCT/AU98/00573

§ 371 (c)(1),
(2), (4) Date: May 9, 2000

(87) PCT Pub. No.: WO99/04620

PCT Pub. Date: Feb. 4, 1999

(30) Foreign Application Priority Data

Jul. 22, 1997 (AU) .................................. PO8174

(51) Int. Cl.[7] .............................. A01H 1/00; A01H 5/00
(52) U.S. Cl. ........................ 800/314; 800/266; 800/298
(58) Field of Search ................................. 800/314, 276, 800/298, 290, 266; 435/419, 320.1; 536/23.6

(56) References Cited

FOREIGN PATENT DOCUMENTS

AT        683830/1997        11/1997

OTHER PUBLICATIONS

Ronald G. Duggleby, Identification of an acetolactate synthase small subunit gene in two eukaryotes, 1997, Gene 190, 245–249.*

Ya. V. Rashkes et al, Sterol and Triterpenoid Content of the Leaves and Leafstalks of Leaf–Shedding Plants and the Standard Line of Cotton, 1989, Khim, Prir., Soedin., vol. 6, pp. 796–805.*

Maxwell et al, Breeding Plants Resistant to Insect, 1980, Wiley–Interscience Publication, pp. 338–369.*

R.J. Kohel, Genetic Analysis of Fiber Color Variants in Cotton, Sep.–Oct. 1985, Crop Science, vol. 25, pp. 793–797.*

Ya. V. Rashkes et al., UDC 547.92+633.511+543.61, "Sterol and Triterpenoid Content in the Leaves and Leaves and Leaf Stalks [Petioles] of Deciduous and Standard Cotton–Plant Varieties", 11 pages, (1989).

* cited by examiner

Primary Examiner—Amy J. Nelson
Assistant Examiner—David H Kruse
(74) Attorney, Agent, or Firm—Foley & Lardner

(57) ABSTRACT

A self-defoliating cotton plant is provided, as are its progeny, reproductive material, seeds, cuttings, seedlings, protoplasts, leaves, stems, flowers, and cotton. In particular, a cotton plant is provided that comprises a nucleic acid sequence as shown in SEQ ID NO: 2 or functional fragments of this nucleic acid. The nucleic acid may be activated by chemical treatment and/or irradiation to effect self-defoliation. Self-defoliation advantageously obviates the need to apply defoliants prior to harvesting.

8 Claims, 5 Drawing Sheets

(1 of 5 Drawing Sheet(s) Filed in Color)

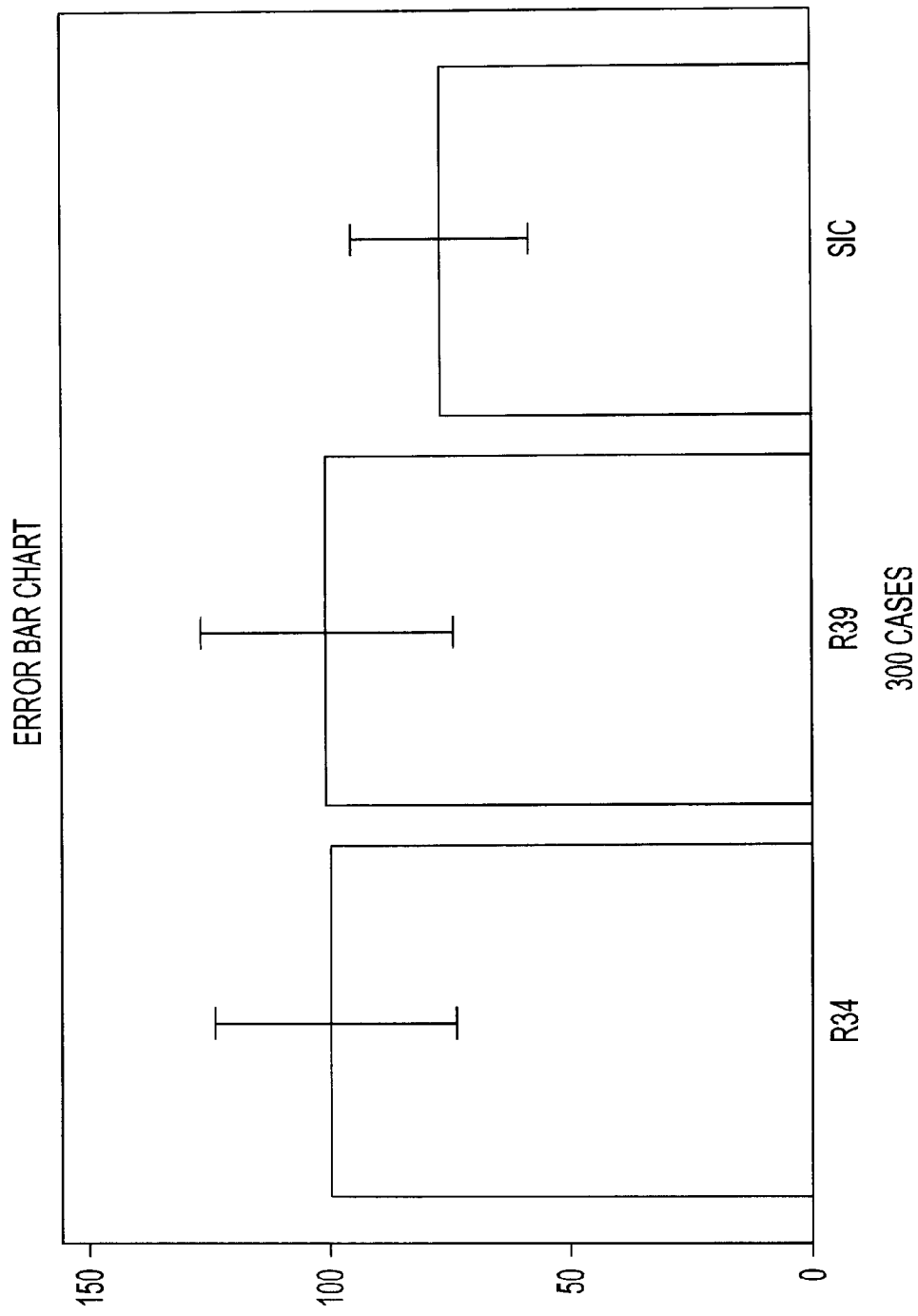

SELF-DEFOLIATING PLANT

This is the National Stage of International Application No. PCT/AU98/00573, filed Jul. 20, 1998.

This invention relates to plants of cotton (*Gossypium hirsutum* L) having new and improved characteristics, and in particular to cotton plants which have the property of self-defoliation. The invention also relates to the gene or genes which determines the self-defoliating property.

BACKGROUND OF THE INVENTION

The production of cotton is a major industry in many countries, including Australia. All cotton fibre is produced from plants of the genus Gossypium. The most commonly grown cotton plants are varieties of *Gossypium hirsutum* (American Upland cotton), which produces fibres of medium staple length, and these are grown in the United States, Australia, Pakistan and other countries where extensive irrigation is available. Egyptian cotton, which has a finer, longer fibre, is produced from *Gossypium barbadense*, grown extensively in Egypt and Sudan. *Gossypium herbaceum* and *Gossypium arboreum* are grown in unirrigated areas of India, Pakistan and other Asian countries, and produce coarser, shorter fibres.

The purity of commercial seed stocks is carefully controlled to avoid problems resulting from crossing between varieties or seed mixing.

However, the cultivation of cotton plants traditionally has required high-intensity agricultural practices, including heavy irrigation, and the application of a number of pesticides. Cotton plants are prone to disease and to infestation by a variety of insect pests, such as Heliothis caterpillar, and the various species of cotton boll-worms, and hitherto control of these pests has required intensive use of chemical insecticides. Furthermore, because of the requirements of mechanical harvesting, defoliants are applied just before harvest in order to remove the leaves from the plant so as to render the cotton bolls easily accessible to the harvesting machinery.

Consequently the cotton-growing industry has been the cause of considerable environmental pollution, and the industry is under great pressure to reduce release of chemicals into the environment. Integrated pest-management practices are increasingly being used, and cotton plants genetically engineered to be resistant to disease or which express *Bacillus thuringiensis* toxin, a natural insecticide of bacterial origin, are becoming available to commercial cotton growers. However, hitherto there has been no alternative to the use of chemical defoliants before harvest.

Whilst wild species of perennial cotton such as *G. aridum* genom D4, *G. gossypioides* D6 and *G. trilobum* D are said to lose leaves acquired during the rainy season when the dry season arrives, this self-defoliation to date has not been found in cotton strains grown commercially.

For many years, traditional breeding methods have been used in an endeavour to identify and select strains of cotton which have improved resistance to the major insect and fungal pests which attack these plants, or which have other desirable characteristics. In parallel, breeding programs have also been directed to the production of self-coloured cotton, which does not require the use of chemical dyes during textile processing.

Professor Victor Fursov, a member of the Academy of Technological Science of the former Soviet Union, commenced cotton plant development programs in March 1962. The program between 1962 and 1993 involved the development of a strain of cotton with specific characteristics, bred and tested under commercial conditions. These included strains of cotton in varying colours of green, beige, brown and "snow white". Surprisingly, the beige and brown self-coloured strains were found to have superior resistance to major insect and fungal pests and had bactericidal properties.

Further development, generation of strains and selection carried out in Australia identified certain strains which have the property of self-defoliation, and which do not need application of chemical defoliation agents.

SUMMARY OF THE INVENTION

In one aspect, the invention provides a self-defoliating cotton plant. In one embodiment, the plant has a gene or functional fragment thereof which is activated to effect self-defoliation of the cotton plant.

In a particularly preferred embodiment, there is provided a strain of cotton (*Gossypium hirsutum*) characterised in that the plants self-defoliate at the stage of boll opening.

The present invention further provides a self-defoliating plant which includes a nucleic acid or functional fragment thereof which is activated to effect self-defoliation of the cotton plant.

In a second aspect, the invention relates to a self-defoliating cotton plant having a DNA fingerprint as shown in FIG. 3. The plant comprises a nucleic acid sequence which determines self-defoliation of cotton (defoliating gene), which gene can be activated by chemical treatment and irradiation. Preferably the nucleic acid sequence comprises the sequence set out in SEQ ID NO:2. More preferably, the gene is activated by treatment with ethylene imine (Aziridine) and ionising radiation.

In a third aspect, the invention provides a method of activating a defoliating gene in cotton, comprising the step of treating the seed of said cotton with ethylene imine and ionizing radiation. Preferably, hybrid seeds produced by crossing of parent cotton plants which have been selected for desired characteristics or traits are treated with 0.1% v/v aqueous ethylene imine for 10 hours, followed by gamma-irradiation of said seeds with 20 kiloroentgens absorbed dose, with a preferred dose of 4 kiloroentgen for 50 seconds. The irradiation may be suitably effected by exposure of the seeds to a Cobalt 60 gamma-ray source, such as MPX-gamma 3.

In a fourth aspect the invention relates to cotton plants which exhibit self-defoliation. The gene for self-defoliation may be activated by chemical and radiation methods, or may be inherited from a parent plant.

Preferably the cotton fibres are of a colour selected from the group consisting of beige, snow-white, brown and green. Also preferably the cotton plants are resistant to one or more diseases caused by *Thielaviopsis babicola, Fusarium vasinfectum* and/or *Bemisia tabaci*.

In a particularly preferred embodiment, the plant is of a variety selected from the group consisting of Rainbow 34, Rainbow 39, Rainbow 38 and Rainbow 37, as herein described. It will be clearly understood that these varieties have colours of the cotton fibres as the principal characteristic differentiating between them.

The whole plants, seeds, and other reproductive material derived from the plants, including cuttings and protoplasts, all form part of the invention. In addition, products derived from the cotton plants, including cotton fibres and textiles produced therefrom, also form part of the invention.

In a separate aspect, the invention provides cotton plants which have been transformed with the self-defoliation gene of the invention. In particular, genetically-engineered strains of cotton and methods for their production are known. There are a number of patents and literature publications by workers from Agracetus and Monsanto describing methods for transformation of cotton, and transgenic cotton plants expressing exogenous proteins such as *Bacillus thuringiensis* crystal protein. Such transgenic cotton plants have been widely field tested, and some strains are in commercial production.

For the purposes of this specification, the term "self-defoliation" is to be understood to mean the self-shedding of foliage and/or leaves from the lower sections of the plant to the higher points, between the period of the growth cycle from 110 days to 135 days, at which time watering can delay the cycle.

Full boll opening occurs at approximately 110 to 135 days.

The terms "activated" and "activating" are to be understood to mean the conversion of the dormant gene for defoliation to one the expression or expression product of which contributes to self-defoliation of a plant containing such a converted gene. The activation includes unblocking of a dormant gene by mutation or by removal of a blocking agent, or by inhibition of an activity thereof. It also includes the inheritance of a gene that was previously activated in the manner described above.

Throughout the description and claims of this specification, the word "comprise" and variations of the word, such as "comprising" and "comprises", means "including but not limited to" and is not intended to exclude other additives, components, integers or steps.

DETAILED DESCRIPTION OF THE INVENTION

The file of this patent contains at least one drawing executed in color. Copies of this patent with color drawing (s) will be provided by the Patent and Trademark Office upon request and payment of the necessary fee.

The invention will now be described in detail by way of reference only to the following non-limiting examples, and to the figures, in which:

FIG. 1 comprises photographs of plants of the preferred embodiments of the invention, "Rainbow 34" (FIG. 1A) and "Rainbow 39" (FIG. 1B).

FIG. 4 is a bar graph showing the results of one way analysis of variance of Rainbow 34, Rainbow 39 and Sicala-34.

EXAMPLE 1

Figure 1A:
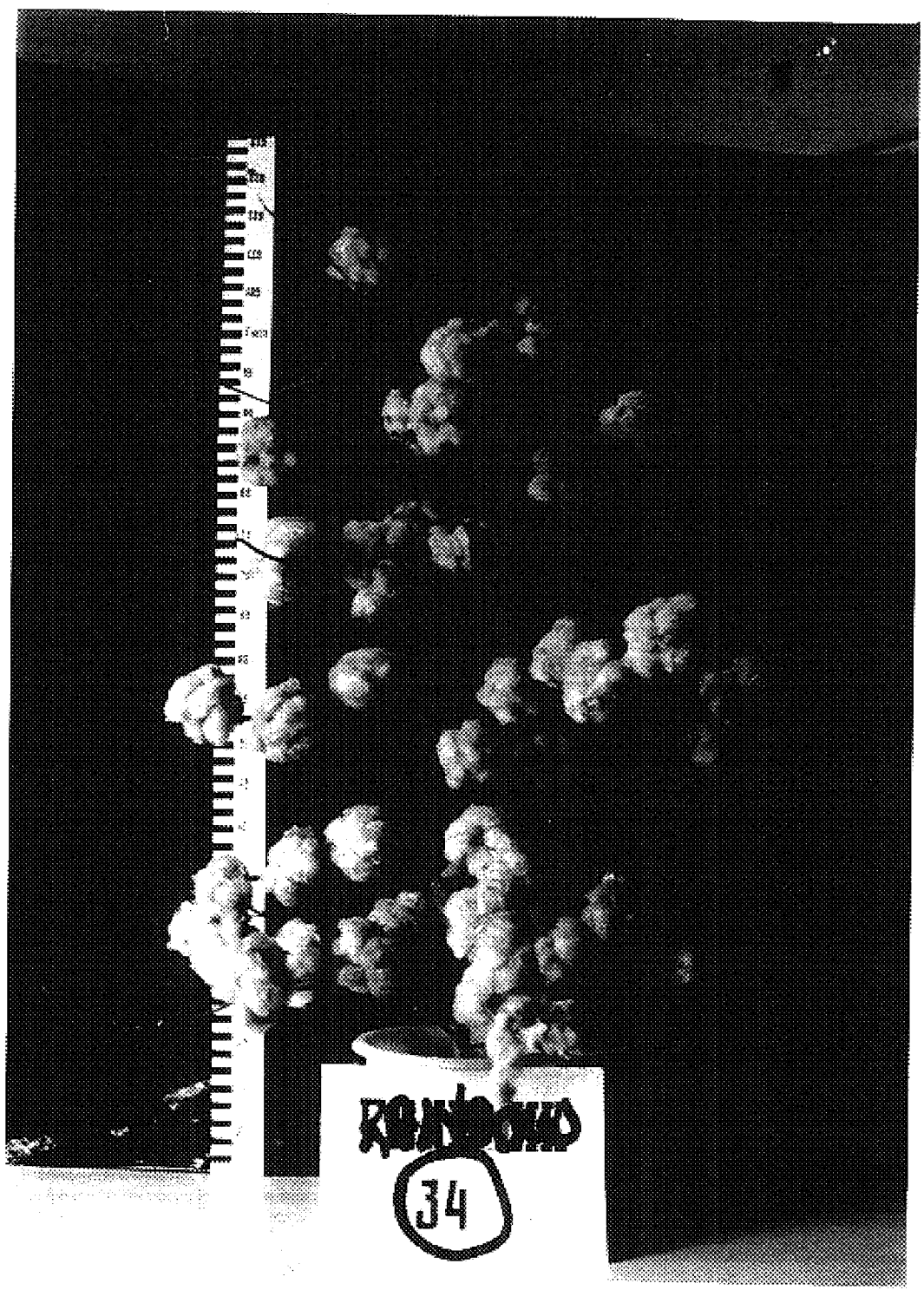

Production of Hybrid Seeds for Activation of the Gene for Defoliation

Analysis of the genealogical data on cotton plants suggested that crossing of the initial parental varieties, 5476 I and 7631 I, was likely to produce white and light beige fibre with high spinning and technological parameters in the hybrid progeny.

The selected elite or P seeds were first subjected to reciprocal hybridisation of not less than 1000–1500 pollinated flowers at 75 per cent setting of seeds in each variant, and F2 plants were crossed with F3 plants. In the second hybrid generation, desired characteristics were selected by sowing seeds and subjecting the plants to the progeny test pedigree method which is familiar to one skilled in the art. Separate sibs were picked from the heterogene complex, and posterities were developed, with strict determination of the principal characteristics. In particular, resistance to fungal and bacterial disease and to insect pests, and colour of the cotton fibre, were used as selection criteria. This selection program was carried out in Russia from 1978 to 1993, and in Australia from 1995 to 1996 under a contract arrangement with the University of Sydney.

Uniform families were crossed to form a new variety, "Genetic 1" bred by Professor Fursov at the Russian Academy of Technological Science, which was deposited in the selection catalogue of the Institute of Cotton Selection of Turkmenistan in 1978. This variety was selected for the technological and spinning qualities of the cotton fibre which it produces.

EXAMPLE 2

Treatment of Hybrid Seeds and Selection for Self-Defoliation

The hybrid seeds produced as described in Example 1 were treated by exposure to 0.1 per cent aqueous ethylene imine for 10 hours.

Ethylene imine was used in concentrations of 0.025–0.05, and 0.1–0.4% (v/v) in water.

Application of various concentrations of this mutagen resulted in different degrees of mutation. After treatment, the quantitative analysis and qualitative analysis of the degree of mutation showed that the mutagen had the greatest effect in "young", recently selected varieties, but hybrids also gave an especially high yield. The more heterogeneous a genotype, the more mutations were observed at a given level of mutagen. The optimum concentration of ethylene imine was 0.1%.

Following treatment with 0.1% ethylene imine for 10 hours, the hybrid seeds were gamma-irradiated using a Co 60 source at a dose of 20 kiloroentgens using the gamma-ray source, MPX-gamma 3-, with 4 kiloroentgen for 50 seconds. The cotton seeds were also irradiated with multiple doses of gamma-irradiation, at levels of −0.25–0.05, −1.0–2.0, −3.0–5.0. Doses of 10.0–20.0 were semi-lethal, and doses of 30.0–60.0 were superlethal. In storage, however, the semi-lethal doses were not totally harmful, and the recovery of the seeds was carefully observed.

The treated seeds were placed in gauze sacks and stored for 18 months at ambient, indoor temperatures.

After 18 months of storage, the selected family seeds were sown into a third hybrid generation, and the elite plants including those manifesting the ability to self-defoliate were selected and crossed between each other. The stored seeds were sown in summer and picked in autumn, with each plant contained in separate sacks. The percentage of deformation was determined as the frequency of phenotypic change, modification of morphology, teratism and other non-hereditary, new growths due to the gamma radiation. After selecting and recording variations in phenotype and any visible changes resulting from mutation, the seeds which gave rise to each phenotype were individually ginned and kept as separate families for sowing the following year.

The genealogical scheme for producing a cotton plant in accordance with the invention is summarised as follows:

F3 (7631-$I$×5476-1)×F2 (5476-$I$×7631-$I$)

Natural hybrid progeny of these parents were then treated with 0.1 per cent ethylene imine for 10 hours. Seeds were selected from the treated population to form seminal M2 and M3 generations. The best lines from these were then crossed.

EXAMPLE 3

Reproduction of Self-Defoliating Cotton Producing Coloured Fibres; The "Rainbow" Series The best lines of seeds treated in the manner described in Example 2 were top crossed and the most significant maternal form of 4 strains were selected. The rest of the strains were hybridized as paternal forms.

The first generation genetic characteristics of self-defoliation were determined by phenotypic domination. All were gathered by individual selection. In the second generation, the population heterogeneity or heritability coefficient was determined. The polygenicity resulted in display of the dominant phenomenon in the first generation hybrid.

This selection method was used to produce a variety of cotton with natural white and light beige fibre with full self-defoliation, such as Rainbow 34 [light beige] and Rainbow 39 [white].

Two other strains, respectively designated Rainbow 38 and Rainbow 37, were also selected for development. The characteristics of these varieties are set out in Table 1.

TABLE 1

Characteristics of Preferred Strains of The Invention

| | Rainbow 34 | Rainbow 38 | Rainbow 37 |
|---|---|---|---|
| Shape | Spreading | Spreading | Spreading |
| Foliage density | Medium | Medium | Medium |
| Height (av.) | Medium–Tall 92 cm | Medium–Tall 60–112 cm | Medium–Tall 68–105 cm |
| Nodes Per Branch (av.) | 5–6 | 2–5 | 2–5 |
| Branch Length (av.) | Long - 44 cm | Long - 46 cm | Long - 45 cm |
| Leaf Shape & Size (av.) | Palmate 17700 mm$^2$ | Palmate 15400 mm$^2$ | Palmate 16080 mm$^2$ |
| Glands/Nectar | + | + | + |
| Flower Petal Colour | Cream | Beige | Beige |
| Fibre Colour | Beige | Brown | Green |
| Boll Size (av.) | 46 mm × 32 mm | 48 mm × 34 mm | 50 mm × 32 mm |
| Boll Shape | Elliptical | Elliptical | Elliptical |
| Boll Lint Content | High | High | High |
| Boll Lint Colour | Cream | Brown | Green |
| Fibre Length (av.) | 36 mm | 35 mm | 35 mm |
| Fibre Fineness (av.) Units? | Fine 3.65 | Fine 3.88 | Fine 3.80 |
| Self Defoliate at Boll Opening | 94% | 89% | 91% |

Figure 1B:
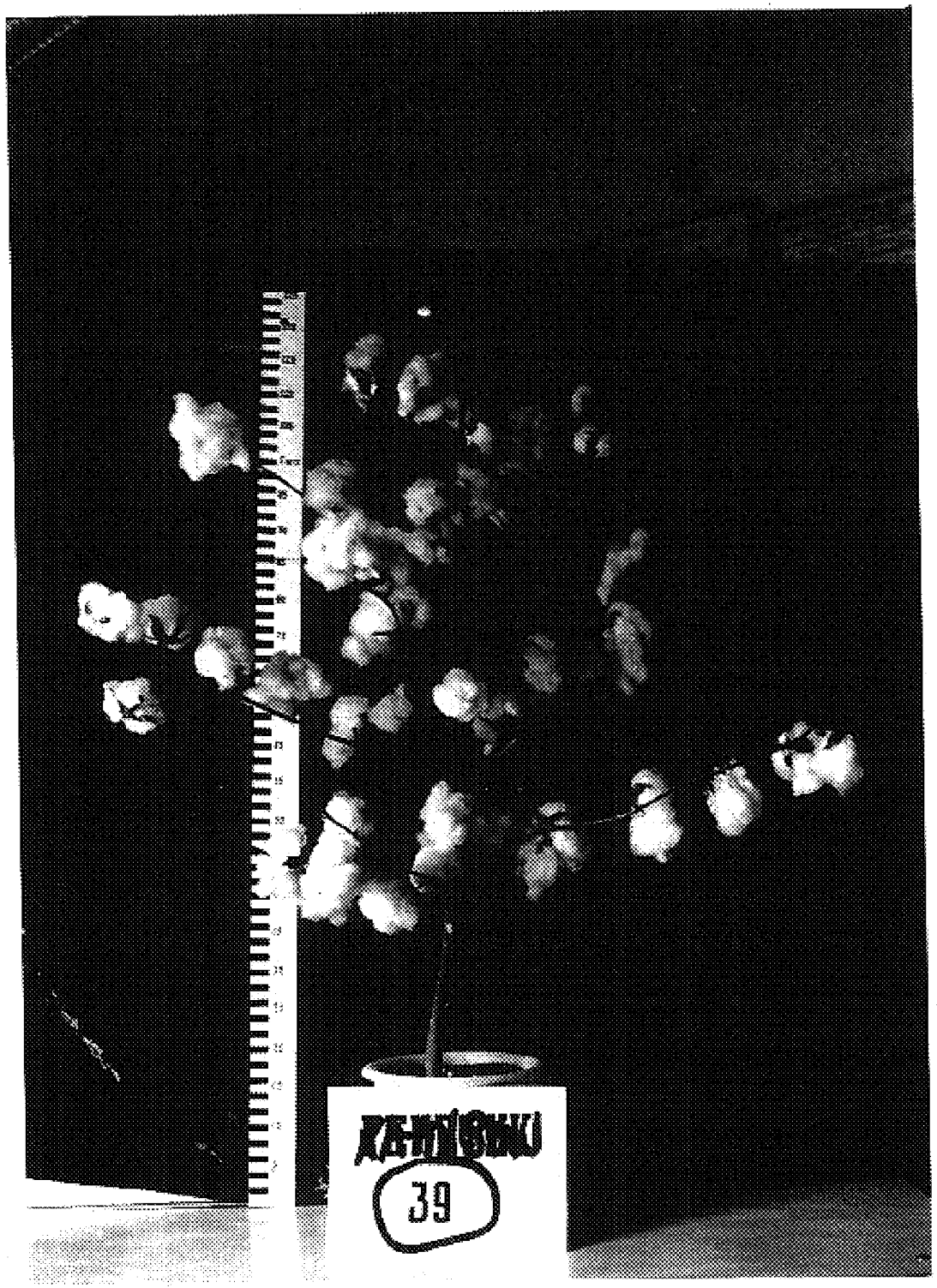
Figure 2:
FIG. 2 illustrates the manner in which Rainbow 39 self-defoliates at the time of opening of the cotton bolls, compared with a non-self defoliating comparator strain, Sicala-34.

Plants of strains Rainbow 34 and Rainbow 39 are illustrated in FIG. 1, and the manner in which Rainbow 39 loses its leaves at the time of boll opening is illustrated in FIG. 2.

It is practicable to repeat the invention using current state of the art techniques to carry out the number of trials necessary to achieve the desired result. Samples of seed Rainbow 39 were deposited under the provisions of the Budapest Treaty with Australian Government Analytical Laboratories on Jul. 2, 1998 and accorded the accession number NM 98/06259. These seeds are also held in the depositary of The University of Sydney, Plant Research and Quarantine Station at Cobbitty, N.S.W., Australia.

The general principles of the method of selecting white and mutant coloured and self-defoliating cotton and methods of defining self-defoliation were as follows:

First Year

To reproduce cotton in the initial form of two species *G. hirsutum* and *G. peruvianum* Cav, the treatment described in Example 2 was applied to the progeny, and dominant mutants manifesting early natural defoliation genotypes by any character were selected.

During the first year, any initial form or variety was produced, so that the total number of seeds with the selected traits would be not less than $10^5$–$10^6$ in the heterogenous population of the variant. Following treatment with the mutagen 1.4 bisdiazoacetyl butane in aqueous solution of 0.1 per cent (v/v) concentration for 20 hours, seeds were washed clean in running water for 2 hours and a sample sowed by placing in highly fertile ground, with 3 seeds in each hole at a depth of 4–5 cm. The soil temperature at a depth of 4–5 cm is preferably 12–15° C. The plot desirably contains 3 plants in a plot 60 cm×20–25 cm or 3 plants in a plot of 90 cm×15 cm.

After shoots appeared, only 2 plants were left in the hole. When two real leaves appeared, the plot was further thinned out to only one plant in the hole.

During growth of the plant, surveys and phenotyping during development were conducted to reveal donor forms and label them for later selections.

During the period of blossoming and ripening of the bolls, all morphological variations of flower, leaf, tomentum of stem, pollen colour, and boll shape were compared with those from non-treated plants, and findings were recorded.

When bolls opened, all clonal forms of mutation were chosen by individual selections. The collected material was analysed, ginned and stored until the next year.

Second Year

The individual seeds showing characteristics selected in the first year were stored and then sown in the second year, with the purpose of selecting multiple mutations, caused by meiosis in comparison with normally formed seeds not treated with mutagens. Morphological observations and self-defoliation dynamics test were then conducted.

The percentage index of timely defoliation is very important: Firstly, the phenomenon should be visually and clearly characterised.

Secondly, a quantitative index is desirable for any comparison or dispersion factor analysis.

The harvest from the selected self-defoliating plants was picked by individual selection, and analysed for boll mass, fibre yield, wave length, fibre index, 1000 seeds mass, metric number, filament breaking strength, sinuosity, lustre, colour etc. The seeds were stored until sowing in the next year.

Third Year

Among selected self-defoliated and other donor forms, consistency and genetic purity tests were carried out during the third year of growth. The percentage of hereditary, homologous mutant lines as determined. All of these lines were chosen by individual selection, and a laboratory grade quality test was also performed.

Fourth and Following Years

After the final study of prospective and competitive new lines, comprehensive varietal grade testing was conducted, and stable forms were carefully examined to ensure that the required characteristics of early, natural defoliation, white and naturally coloured fibre etc. were maintained.

These characteristics usually demonstrated consistency at the beginning of the third growth year. With precise sowing diaries, the degree of any weak character or contaminated species was marked in families. Then the breeding study (selection) was carried out using two subsequent gradings of excellent characteristics which were displayed. Families with any poor characteristics or which were susceptible to attack by whiteflies were rejected, and further selection of these terminated.

Remaining plants were simultaneously selected from the most reproducible families, and used for testing of varietal purity and to ensure continued resistance to damage by whiteflies.

The most superior breeding lines were planted for grade testing and studying against an artificial provocative background. For this purpose, 10 samples of bolls were taken for complex analysis. Selected group families then provided 2.5–3.0 kg of pure grade seeds and were frozen for future use.

The cotton defoliation percentage is defined in two ways:

1. The ratio of defoliated leaves on the main stem (the number of fruit node leaf ribs) to the total number of the formed ones, including already fallen leaves on the main stem by the fixed time in per cent.

These ratios can be expressed by formulae:

$$D = \frac{Cf}{F} \times 100 \text{ per cent (defoliation for one plant)}$$

$$D = \frac{Cf}{CF + con\ f} \times 100 \text{ per cent at } F = Cf + con\ f$$

where:

D Defoliation

Cf Number of leaf ribs (from Latin-cicatris folii

F Total number of leaves con f Dead leaves and preserved leaves

Self-defoliation of cotton most desirably occurs coincidentally with the time of full boll opening and ripeness, and the earlier this characteristic is detected, the more commercially useful.

In the second generation, stable, constant elite plants with early natural self-defoliation were selected. They represented dominant and recessive mutations, which can be progenitors of self-defoliating cotton varieties, without the unblocking of the gene. Those exhibiting early natural self-defoliation were designated as "Fc", from the Latin folium caolucus (fallen leaf).

The chemical-mutagenesis method of the invention permits rapid, ordinary selection of progressive mutations.

Furthermore, the greatest probability of efficient induction of self-defoliation is ensured by chemical action of agents having chemical affinity for DNA. Without wishing to be bound by any proposed mechanism for the observed advantages, it is believed that the affinity of a chemical such as ethylene imine together with irradiation reverses the blockage of the dormant or "sleeping" defoliating gene (dominant as well as recessive), thereby activating it.

It is practicable to repeat the invention using current state of the art techniques to carry out the number of trials necessary to achieve the desired result.

Additional data of the invention are given in Tables 2 to 5.

TABLE 2

Comparison of Gossipium varieties.
1995 "Rainbow 39" and Comparator (*)

|  | Variety Name RAINBOW-39 | Comparator: SICALA-34‡ |
|---|---|---|
| Plant Height (mm) |  |  |
| mean | 1305.0 | 778.00 |
| std deviation | 156.99 | 169.85 |
| LSD(0.01)/significance | 120.18 | P ≦0.01 |
| ⌐Leaf Shape: | Palmate | Palmate |
| ⌐Leaf: Gossypol glands: | present | present |
| Leaf: Nectaries | present | present |
| Flower: Colour | cream | cream |
| Ball Size cm³ (1) |  |  |
| mean | 39.90 | 30.70 |
| std deviation | 9.899 | 6.292 |
| LSD(0.01)/significance | 2.674 | P ≦ 0.01 |
| Ball: Shape | elliptic | elliptic |
| Ball Shape H/W (2) |  |  |
| mean | 1.8765 | 1.587 |
| STD deviation | 0.1618 | 0.1114 |
| LSD(0.01)/significance | 2.674 | P ≦ 0.01 |
| Peduncle Length (mm) |  |  |
| mean | 11.20 | 18.50 |
| std deviation | 1.8525 | 2.0283 |
| LSD(0.01)/significance | 2.674 | P ≦ 0.01 |
| Fibre colour: | white | white |
| PLANT HEIGHT (mm) |  |  |
| mean | 906.70 | 910.4 |
| std deviation | 127.91 | 158.64 |
| LSD 0.01/significance | 47.13 | NS |
| LEAF WIDTH (mm) |  |  |
| mean | 161.72 | 142.1 |
| std. deviation | 21.76 | 18.53 |
| LSD 0.01/significance | 7.98 | P ≦ 0.01 |
| LEAF HEIGHT (mm) |  |  |
| mean | 124.72 | 108.10 |
| std. deviation | 16.11 | 14.51 |
| LSD 0.01/significance | 5.35 | P ≦ 0.01 |
| BOLL HEIGHT (mm) |  |  |
| mean | 52.79 | 47.45 |
| std. deviation | 4.73 | 5.76 |
| LSD 0.01/significance | 1.97 | P ≦ 0.01 |
| BOLL SHAPE (height/width ratio) |  |  |
| mean | 1.38 | 1.37 |
| std. deviation | 0.095 | 0.174 |
| LSD 0.01/significance | 0.0486 | NS |
| PEDUNCLE LENGTH (mm) |  |  |
| mean | 26.24 | 27.37 |
| std. deviation | 5.323 | 7.15 |
| LSD 0.01/significance | 2.085 | NS |
| LINT (%) |  |  |
| mean | 31.8 | 35.98 |
| std. deviation | 1.41 | 3.71 |
| LSD 0.01/significance | 5.32 | NS |
| FIBRE LENGTH (ins) |  |  |
| mean | 1.26 | 1.142 |
| std. deviation | 0.0182 | 0.024 |
| LSD 0.001/significance | 0.0607 | P ≦ 0.01 |
| FIBRE STRENGTH (g/tex) |  |  |
| mean | 32.24 | 46.58 |
| std. deviation | 2.51 | 2.5094 |
| LSD 0.001/significance | 7.73 | P ≦ 0.01 |

TABLE 2-continued

Stability

| Charac-teristic | Breeders' infor-mation | Mean or state for Generation 1 | Mean or state for Generation 2 | Difference between the means | Same (S) (D)? |
|---|---|---|---|---|---|
| Deciduous | yes | yes | yes | | S |
| Leaf: shape | palmate | palmate | palmate | | S |
| Leaf: gossypol glands | present | present | present | | S |
| Leaf: nectaries | present | present | present | | S |
| Flower: colour | cream | cream | cream | | S |
| Boll: shape | elliptic | elliptic | elliptic | | S |
| Lint: colour | white | white | white | | S |

Uniformity - cross-pollinated species
The following variance ratios are submitted as evidence of uniformity:

| Charac-teristic | Variance of new variety: 'Rainbow - 39' | Variance of reference variety: 'Sicala-34' | Ratio new/reference |
|---|---|---|---|
| Plant height | 16360 | 25090 | 0.65 |
| Boll length | 22.28 | 33.18 | 0.67 |
| Boll shape | $9.025^{-03}$ | 0.029 | 0.31 |
| Peduncle length | 28.3 | 51.12 | 0.55 |
| Line % | 0.74 | 4.88 | 0.15 |
| Fibre length | $3.31^{-04}$ | $6.2^{-04}$ | 0.53 |

(1) Ball size indicated by volume of a theoretical cylinder in which the oldest unopened ball would fit in
(2) Ball shape denoted by Height/width ratio
(*) In Quarantine Greenhouse
(* = comparator)

TABLE 3

Comparison of Gossipium varieties. 1996 "Rainbow 39"

| | Variety Name RAINBOW-39 | Comparator: SICALA-34* |
|---|---|---|
| Plant Height (mm) | | |
| mean | 906.70 | 910.4 |
| std deviation | 127.91 | 158.64 |
| LSD(0.01)/significance | 47.134 | NS |
| Leaf size cm² (1) | | |
| mean | 101.44 | 77.93 |
| std deviadon | 26.008 | 18.904 |
| LSD(0.01)/significance | 8.61 | $P \leq 0.01$ |
| Leaf Shape: | Palmate | Palmate |
| Leaf Shape W/H (2) | | |
| mean | 1.31 | 1.33 |
| std deviation | 0.1022 | 0.1551 |
| LSD(0.05)/significance | 1.968 | NS |
| Leaf: Gossypol glands: | present | present |
| Leaf: Nectaries | present | present |
| Flower: Colour | cream | cream |
| Ball Size cm³ (3) | | |
| mean | 62.855 | 47.092 |
| std deviation | 15.842 | 11.713 |
| LSD(0.01)/significance | 2.593 | $P \leq 0.01$ |
| Ball: Shape | elliptic | elliptic |
| Ball Shape H/W (4) | | |
| mean | 1.3818 | 1.3610 |
| STD deviation | 0.0948 | 0.1726 |
| LSD(0.01)/significance | 2.593 | NS |
| Peduncle Length (mm) | | |
| mean | 26.24 | 27.25 |
| std deviation | 5.3227 | 7.0559 |
| LSD(0.01)/significance | 2.593 | NS |
| Fibre colour: | white | white |
| FIBRE MICRONAIRE VALUE | | |
| mean | 2.67 | 3.52 |
| std. deviation | 0.11 | 0.38 |
| LSD 0.01/significance | 0.15 | $P \leq 0.01$ |
| FIBRE EXTENSION (%) | | |
| mean | 5.9 | 6.14 |
| std. deviation | 0.51 | 0.055 |
| LSD 0.01/significance | 0.864 | NS |
| FIBRE UNIFORMITY INDEX (%) | | |
| mean | 89.26 | 87.8 |
| std. deviation | 1.17 | 1.15 |
| LSD 0.01/significance | 3.24 | NS |
| DISCRETE CHARACTERISTICS | | |
| Leaf Shape | palmate | palmate |
| Leaf Gossypol Glands | present | present |
| Leaf Nectaries | present | present |
| Flower: Colour | cream | cream |
| Boll: Shape | elliptic | elliptic |
| Fibre: Colour | white | white |

Uniformity - cross-pollinated species
The following variance ratios are submitted as evidence of uniformity:

| Charac-teristic | Variance of "Rainbow - 39" | Variance of reference variety: "Sicala-34" | Ratio new/combined |
|---|---|---|---|
| Plant Height | 16360.97 | 25166.65 | 0.65 |
| Leaf shape | 0.01 | 0.024 | 0.42 |
| Ball shape | $8.98704^{-03}$ | 0.03 | 0.31 |
| Peduncle length | 28.33 | 49.79 | 0.57 |

(1) Leaf size measured by the area of the triangle created by the height and the width of the oldest leaf
(2) Leaf shape shown by width/height ratio
(3) Ball size indicated by volume of a theoretical cylinder in which the oldest unopened ball would fit in
(4) Ball shape denoted by Height/width ratio

TABLE 4

STATISTIX 4.1
ONE-WAY AOV FOR: R34 R39 SIC

| SOURCE | DF | SS | MS | F | P |
|---|---|---|---|---|---|
| BETWEEN | 2 | 34719.0 | 17359.5 | 31.45 | 0.0000 |
| WITHIN | 297 | 1.639E+05 | 551.927 | | |
| TOTAL | 299 | 1.986E+05 | | | |

| | CHI-SQ | DF | P |
|---|---|---|---|
| BARTLETT'S TEST OF EQUAL VARIANCES | 11.01 | 2 | 0.0041 |

| | | |
|---|---|---|
| COCHRAN'S Q | | 0.4085 |
| LARGEST VAR/SMALLEST VAR | | 1.8928 |
| COMPONENT OF VARIANCE | | 16.076 |

TABLE 4-continued

FOR BETWEEN GROUPS
EFFECTIVE CELL SIZE            100.0

| VARIABLE | MEAN | SAMPLE SIZE | GROUP STD DEV |
|---|---|---|---|
| R34 | 100.00 | 100 | 24.941 |
| R39 | 101.44 | 100 | 26.008 |
| SIC | 77.932 | 100 | 18.904 |
| TOTAL | 93.123 | 300 | 23.493 |
| CASES INCLUDED 300 | | MISSING CASES 0 | |

STATISTIX 4.1
LSD (T) PAIRWISE COMPARISONS OF MEANS

| VARIABLE | MEAN | HOMOGENEOUS GROUPS |
|---|---|---|
| R39 | 101.44 | I |
| R34 | 100.00 | I |
| SIC | 77.932 | . . . I |

THERE ARE 2 GROUPS IN WHICH THE MEANS ARE
NOT SIGNIFICANTLY DIFFERENT FROM ONE ANOTHER.
CRITICAL T VALUE    2.592    REJECTION LEVEL    0.010
CRITICAL VALUE      8.6133
FOR COMPARISON
STANDARD ERROR      3.3224
FOR COMPARISON

STATISTIX 4.1
DESCRIPTIVE STATISTICS

| | R34 | R39 | SIC |
|---|---|---|---|
| N | 100 | 100 | 100 |
| MISSING | 0 | 0 | 0 |
| SUM | 1.000E+04 | 1.014E+04 | 7793.2 |
| LO 95% CI | 95.054 | 96.275 | 74.181 |
| MEAN | 100.00 | 101.44 | 77.932 |
| UP 95% CI | 104.95 | 106.60 | 81.683 |
| SD | 24.941 | 26.008 | 18.904 |
| SE MEAN | 2.4941 | 2.6008 | 1.8904 |
| C.V. | 24.940 | 25.640 | 24.257 |
| MINIMUM | 51.920 | 51.300 | 43.610 |
| 1ST QUARTI | 84.025 | 83.585 | 64.190 |
| MEDIAN | 94.400 | 99.120 | 78.100 |
| 3RD QUARTI | 109.20 | 111.24 | 91.412 |
| MAXIMUM | 183.06 | 222.00 | 131.95 |
| MAD | 11.800 | 13.650 | 13.845 |
| BIASED VAR | 615.81 | 669.63 | 353.78 |
| SKEW | 1.0511 | 1.6782 | 0.3960 |
| KURTOSIS | 1.3222 | 5.0449 | −0.2032 |

TABLE 5

COTTON
*Gossypium hirsutum*
'Rainbow - 39' synonym: 'Genetic 39'.

Description:

Plant: spreading; medium to tall height; dense foliage;
the fruiting branches are long.
Leaves: palmate with pubescent midrib and also have gossypol
glands and nectaries and are deciduous at maturity . . .
Flowers: cream. Bolls are elliptic with long 26.24 mm peduncles.
Fibre length is 1.26 ins when ginned with the "shark-skin"
method.
Fibre: uniformity index 89.26%, elongation 5.9%, strength 32.24
g/tex and micronair value is 2.7.
Origin:

Induced mutation by radiation used on seed of breeding
line 'Turkmenistan Genetic 1'.

TABLE 5-continued

COTTON
*Gossypium hirsutum*
'Rainbow - 39' synonym: 'Genetic 39'.

Breeder: Professor V. N. Fursov, Ashgabat, Turkmenistan.
In the following generations pedigree method was used
to select early maturing, self defoliating plants with
long staple length until the stable variety was established.
Comparative Trials.

Comparator: Sicala-34. Conducted in 1994/95 in the greenhouse
of the Commonwealth Quarantine Station, Rydalmere and in
1995/96 at The University of Sydney, Plant Breeding Institute,
Narrabri. Measurements were taken from 95 plants selected at
random from a trial arranged in randomised complete blocks
in four replicates. The fibre quality data were acquired
from lint obtained by "shark-skin" ginning and the
tests were replicated five times. Greenhouse grown plants
also displayed long fibre length.

Adaptation
'Rainbow - 39' can be grown in any district where cotton could be produced

EXAMPLE 4

Other Embodiments

Interspecific hybrids—previously in F1—treated with ethylene imine in 5 concentrations of aquatic solution with control variant, were sown in an area of 0.25 hectares.

Then in laboratory trials, F3-Chem3, the breeding strains/progenies of the newly obtained variety were grown, repollinated by the top cross method for the best mutant line, combining one each genotype of white or beige colour with 100 per cent self-defoliation.

To define the genetic nature of the defoliation trait of top crosses in F1, the phenotypic domination degree-P was determined.

These F1 hybrids showed dominance of the self-defoliation characteristics of initial forms when crossing the most superior selected self-defoliation mutant lines, breeding the variety herein designated "BD", obtained as the result of the selection method.

In F2 the heritability of the self-defoliation characteristic of hybrids is defined. The degree of heterogeneity in mutation generations and in hybrid F2–F3 populations was determined by the genetic variability or hereditary ability co-efficient which was calculated by the Allard formula:

| | | |
|---|---|---|
| h2 | | hereditary ability coefficient of any character |
| G2 | P1 | first parent dispersion |
| G2 | F1 | hybrids F1 dispersion |
| G2 | P2 | second parent dispersion |
| G2 | F2 | hybrids F2 dispersion |

$$h2 = \frac{G2\ F2 - \frac{G2\ F1 + G2\ P1 + G2\ P2}{3}}{G2\ F2}$$

EXAMPLE 5

DNA Fingerprint of Rainbow 39

DNA extracted from Rainbow 39 was compared to DNA of Sicala-34 (the comparator strain) in DNA fingerprint assays performed under contract by the Australian Government Analytical Laboratories, Molecular Biology Laboratory.

Samples of genomic DNA were extracted from two *Gossypium hirsutum* varieties (Rainbow 39 and Sicala 34) by the cetyltrimethyl ammonium bromide (CTPB) method. CTAB is a detergent which disrupts cell walls and forms a complex with nucleic acids. The CTAB-nucleic acid complex can then be purified and separated from carbohydrates (Brian et al 1994, Scott et al 1994). The DNA extracted using the CTKB was then subjected to further purification steps to eliminate inhibitors of DNA polymerase. Firstly, polyvinyl-pyrrolidone (PVP) was added to the CTAB extraction buffer. PVP improves the precipitation of polyphenolics and other organic substances (Kim at al, 1997). Secondly, the final DNA pellets were incubated with InstaGene Matrix™ (BIO-RAD), a commercial DNA purification matrix. This resin-based matrix efficiently absorbs cell lysis products that interfere with the PCR amplification process. The results showed that a satisfactory PCR amplification was achieved using the cotton DNA extracted by this new method. Suitable 10-mer primers for the generation of DNA fingerprints were screened from 40 randomly selected 10-mer primers.

A large amount of genomic DNA is required for the generation of DNA fingerprints for cotton plants. Fresh young leaf tissues therefore are required for the DNA extraction. Cotton leaf tissues that are not fresh have very low levels of DNA, a high level of polyphenolics and other inhibitors.

Extracted DNA was assayed by the technique of Random Amplified Polymorphic DNA Polymerase Chain Reaction (RAPD PCR).

Figure 3:
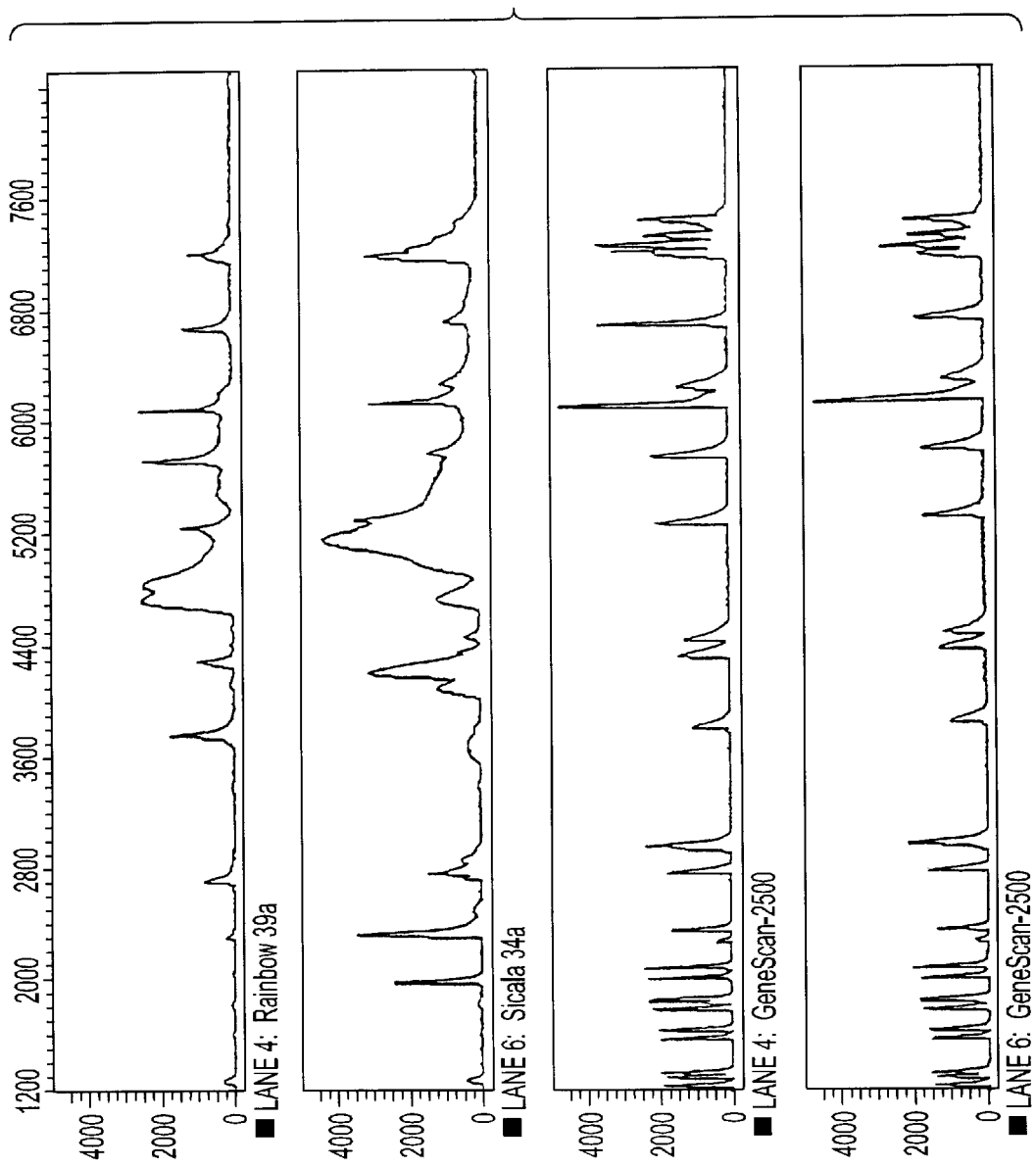
FIG. 3 shows the DNA fingerprint of Rainbow 39 and the comparator strain, Sicala-34.

The DNA fingerprints of RAINBOW 39 and SICKLA 34 showed significant differences when three single primers were employed in RAPD PCR assay although most primers generated identical DNA fingerprints for both RAINBOW 39 and SICALA 34. This indicated that RAINBOW 39 and SICALA 34 are very closely related cotton varieties. However, as shown in FIG. 3, one primer (primer z11) generated reproducibly distinct DNA fingerprints between RAINBOW 39 and SICALA 34. The DNA fingerprint gel profiles generated with primer z11 showed the different RAPD PCR profiles (lanes 4 and 6) between RAINBOW 39 and SICALA 34. The DNA band sizes were indicated by DNA standard GENESCAN-2500.

The protocol for obtaining the DNA fingerprints is given in detail below:

1. Extraction of Genomic DNA From *Gossypium hirsutum*

Deoxyribonucleic acids (DNA) was extracted from fresh young leaf of cotton by the protocol described below.

(1) 250 μg of cotton tissues were ground in a motar with 20 μl of 2-mercaptoethanol (SIGMA, M-3148) until the tissues were of a creamy consistency.

(2) 600 μl of 2×extraction buffer was added to the tissues and was further ground until the tissue solution became clear (2×extraction buffer: 2.0% cetyltrimethylammonium bromide, 1.4 M NaCl, 100 mM Tris-HCl pH 8.0, 20 mM ethylenediamine tetraacetic acid, 1.0% polyvinylpyrrolidone).

(3) The tissue solution was transferred into a 1.5 ml microtube and incubated at 65° C. for 5 minutes.

(4) 600 μl of chloroform/isoamyl-alcohol (24:1) was added into the tissue solution and mixed thoroughly with a vortex mixer to form an emulsion. The microtube was then centrifuged at 10,000×g for 5 minutes.

(5) The solution from the top aqueous phases was transferred into new microtubes each containing 600 μl of isopropanol, and mixed by inversion until the white thread-like strands of DNA formed visible masses.

(6) The microtube was incubated on ice for 10 minutes and centrifuged at 5,000×g for 2 minutes.

(7) The supernatant was removed with a pipette and discarded.

(8) The DNA pellet was hydrated by the addition of 400 μof high-salt TE buffer and then incubated at 65 C for 10 minutes (high-salt TE buffer: 10 mM Tris pH 8.0, 1.0 mM ethylenediamine tetraacetic acid pH 8.0, 1.0 M NaCl).

(9) The DNA was precipitated by the addition of 800 μl of absolute ethanol and mixed by inversion until the white thread-like strands of DNA formed visible masses.

(10) The microtube was incubated on ice for 10 minutes and centrifuged at 5,000×g for 2 minutes.

(11) The supernatant was removed and discarded with pipette.

(12) The DNA pellet was dried at room temperature by leaving the microtube open to air for 1 hour.

(13) The DNA pellet was rehydrated by the addition of 200 μl of 10% (w/v) of Chelex® 100 Resin (BIO-RAD) in TE Buffer and incubated at 55° C. for 30 minutes. (TE Buffer: 10 mM Tris pH 8.0, 1.0 mM ethylenediamine tetraacetic acid pH 8.0).

(14) The rehydrated DNA solution was centrifuged at 12,000×g for 10 minutes.

(15) The DNA supernatant was transferred into new microtubes.

(16) The resin pellet was suspended by 200 μl of TE Buffer and incubated at room temperature for 20 minutes. Steps (14) and (15) were then repeated.

(17) The ribonucleic acids (RNA) were removed from DNA solution by the addition of 2 μl of RNase (20 mg/ml) and the microtube was incubated at 37° C. for 30 minutes.

(18) The DNA concentration and quality were measured by the ethidium bromide fluorescence quantitation method.

(19) The DNA at this stage was used for RAPD PCR assay or stored at 4° C.

2. Random Amplified Polymorphic DNA Polymerase Chain Reaction (RAPD PCR) for the Generation of DNA Fingerprints.

This protocol generated DNA fingerprints by random amplified polymorphic DNA (RAPD) technology, utilizing a single, 10-mer oligonucleotide primer of arbitrary sequence to amplify genomic DNA sequences of cotton *Gossypium hirsutum* varieties (RAINBOW 39 and SICALA 34). GeneScan 672 software was used to analyse the RAPD PCR products.

(i) RAPD PCR Procedure

RAPD PCR was set in a volume of 25 μl with approximately 25 nanograms of cotton genomic DNA, 100 μM of a single 10-mer primer, primer z11:

5-CTCAGTCGCA-3' (SEQ ID NO: 1), 2.0 mM $MgCl_2$ 10 mM Tris-HCl, pH 8.3, 16.6 mM $(NH4)_2SO_4$, 100 μg/ml gelatin, 0.45% Triton-X100, 100 μM dTTP, 100 μM dCTP, 100 μM dGTP, 100 μM dTTP, 0.1 μM dUTP, and 1.0 unit of Taq DNA polymerase (Perkin Elmer). The reactions were performed within a 0.5 ml-microtube overlaid with mineral oil. Amplification was cycled in a thermal cycler (HYBAID, OmniGene, U.K.) preheated to 95° C. The cycler was programmed for 45 cycles of 1 minute at 94° C, 1 minute at 36° C. and 2 minutes at 72° C. on a for DNA denaturing, primer annealing, and primer extension, respectively. The PCR products were stored at −20° C.

(ii) RAPD PCR Generated DNA Fingerprints Were Analysed Using AB1 GeneScan 672 Software on a DNA Sequencer 373 System.

Electrophoresis Conditions

A 4.5% native polyacrylamide gel solution was prepared with 9 ml 40% Acrylamide:N,N'-Methylen-bis-acrylamid=

19:1 stock solution (BIO-RAD), 16 ml of 5×TBE buffer (5×TBE buffer in 1 liter: 54 g Tris base, 27.5 g boric acid, 20 ml of 0.5M ethylenediamine tetraacetic acid pH 8.0), 55 ml of distilled water, 400 μl of 10% ammonium persulfate, and 45 μl of N,N,N',N'-Tetra-methy-ethylenediamine.

The buffer was 1×TBE (280 ml of 5×TBE buffer, 1120 ml of distilled water). Electrophoresis was performed at a voltage of 700 v for 18 hours. RAPD PCR products were diluted with distilled water in 1:10. 1 μg diluted products were combined with 1μ internal lane DNA size standard GeneScan-2500 ROX and 3 μl loading buffer (AB1 GeneScan kit). The combined samples then were loaded on the gels described above. Results of DNA fingerprints were automatically analysed and reported by AB1 373 automatic DNA sequencer with GeneScan 672 software, and are illustrated in FIG. 3.

EXAMPLE 6

Sequencing of Rainbow 39

A 227 bp genomic DNA fragment was amplified from cotton *Gossypium hirsutum* variety (Rainbow 39) using the Polymorphic Random Amplified DNA Polymerase Chain Reaction (RAPD PCR) assay as outlined below. This DNA fragment was not amplified by this assay from another, non-self defoliating cotton variety (Sicala 34). The 227 bp DNA fragment was cloned into a plasmid vector and sequenced using the ABI 373 automatic DNA sequencer. The DNA sequence of the fragment was determined, and is shown in SEQ ID NO:2.

Experimental Protocols
1. PCR by Random Amplified Polymorphic DNA (RAPD) Assay

Genomic DNAs from cotton Rainbow 39 and Sicala 34 varieties were subjected to RAPD-PCR reaction. Each amplification reaction was performed in a volume of 25 μl with approximately 25 nanograms of genomic DNA, 25 ng of a single 10-mer primer, 2.0 MM $MgCl_2$, 10 mM Tris-HCl, pH 8.3, 16.6 mM $(NH_4)_2SO_4$, 100 μg/ml gelatin, 0.45% Triton-X100, 100 μm of each dNTPs, and 1.0 unit of Taq DNA polymerase. The reactions were performed within a 0.5 ml-microtube overlaid with mineral oil. Amplification was programmed for 45 cycles of 1 minute at 94° C., 1 minute at 36° C. and 2 minutes at 72° C. on a thermal cycler for (HYBAID, OmniGene, U.K.) DNA denaturing, annealing, and primer extension, respectively. Blank control (no DNA added in the PCR reaction and replaced with water) was included in each RAPD PCR performance. The PCR products were analysed by electrophoresis on a 1.4% agarose gel and visualised with ethidium bromide staining and photographed.

2. Purification of RAPD PCR Fragments

DNA bands were separated on 1.2% low melting point agarose gels stained with ethidium bromide, and the desired fragment was sliced from the gel. The sliced gel containing the DNA fragment was put into a 1.5 ml Eppendorf tube and covered with TE buffer and then heated for 15 minutes at 70° C. to melt the gel. The melted gel solution was extracted with phenol/chloroform and then with chloroform. The DNA was precipitated by adding 0.1 volume of 3M sodium acetate and 1 volume of isopropanol and incubation at −20° C. overnight. The DNA was collected by centrifugation at 10,000 g for 15 minutes and resuspending the DNA pellet in sterile water. The DNA concentration was measured by running an electrophoresis gel with quantified DNA molecular size markers.

3. DNA Cloning (a) Ligation

The pGEM-T vector (Promega) was also used for cloning the PCR band. Ligation of PCR products using these vectors was carried out according to the manufacturer's instructions.

(b) Transformation

10% of the ligation reaction, or 5 ng of uncut vector for control, was mixed with 100 μl of competent cells in an Eppendorf tube and incubated on ice for 1 hour. The Eppendorf tubes were heat shocked at 42° C. for 2 minutes in a water bath then incubated on ice for 20 minutes. Then 1 ml of LB was added to the tubes and the cells were incubated at 37° C. for 30–40 minutes on a rotating vertical wheel. The bacterial cells were collected by centrifugation at 1,500 g on a minicentrifuge for 10 minutes and resuspended in 200 μl of LB containing 30 mg/ml of X-gal and 20 mg/ml IPTG. The bacterial solution was spread on LB-agar plates containing 100 μg/ml of ampicillin and dried in a 37° C. oven for 2 hours and then the agar plates were inverted and incubated at 37° C. overnight.

(c) Selection of Recombinant Clones

Bacterial colonies containing the recombinant vector were white, while those with non-recombinant vector were blue. Five white colonies were selected for plasmid preparation as described below. The presence of an insert was confirmed by restriction enzyme cleavage to linearize the plasmid and running the products on a agarose gel.

(d) Restriction Digestion Analysis of Inserts

Restriction endonucleases: EcoRI for the pGEM—5Zf(+) vector were used to cut out the insert from the plasmid vector. The cut insert and the vector were then separated on 1.2% agarose gel electrophoresis. A control insert and linearised vector DNA were also run on the same gel. The correct recombinant plasmid was identified by the presence of both insert and vector bands.

4. Plasmid DNA Preparation for DNA Sequencing

A single colony of transformed *E. coli* strain JM109 was cultured in 5 ml of LB broth containing 10 μg/ml of ampicillin at 370° C. with shaking overnight (about 16 hours). Three 1.5 ml aliquots of each sample were pelleted in 1.5 ml Eppendorf tubes by microcentrifugation with 1,500 g for 10 minutes. The *E. coli* pellets were fully resuspended in 200 μl of GET buffer (50 mM glucose/25 mM EDTA/20 mM Tris-HCl, pH 8.0), and were then centrifuged with 1,500 g for 10 minutes. The *E. coli* pellets were resuspended in 50 μl of GET containing 10 mg/ml of lysozyme. After leaving on ice for 30 minutes, the *E. coli* was lysed by the addition of 150 μl of 0.5 M NaOH/1.0% SDS. Proteins and genomic DNA were precipitated by adding 200 μl of 3M potassium acetate pH 5.2. The supernatant was transferred to new Eppendorf tubes. Plasmids were then precipitated by the addition of an equal volume of isopropanol and then centrifuged at 10,000 g for 10 minutes. Plasmid pellets were washed with 70% ethanol and air dried for 1 hour. Plasmid DNAs were dissolved in 200 μl of TE buffer containing 10 μg/ml of RNase and incubated at 370° C. for 1 hour. DNA solutions were extracted twice with Phenol:Chloroform (1:1). Plasmid DNAs were then precipitated by adding 0.1 volume of 3M sodium acetate pH 5.2 and 2.5 volume of absolute ethanol. After incubating on ice for 30 minutes, plasmid DNAs were then centrifuged at 10,000 g for 10 minutes. DNA pellets were washed with 70% ethanol and dried as described above. Plasmid DNAs were finally dissolved in 50 μl of water and stored at −2000.

5. DNA Sequencing

Dideoxy chain termination sequencing was performed on an ABI automatic DNA sequencer (Model 373, UAS) using an AmpliTaq DNA polymerase Dye Terminator Cycle Sequencing Kit according to the conditions recommended by Perkin Elmer. DNA sequence data were obtained using ABI sequencing analysis software.

PREFERRED EMBODIMENT OF THE INVENTION

In a preferred embodiment, the cotton plant of the invention is the variety designated "BD", which has snow-white cotton fibres, and exhibits timely self-defoliation by the end of vegetation.

The variety shows sympodial branching, is a shrub of pyramidal form with 0–2 monopodia shrub heights 100–110 cm, and boll mass about 5.5 g. The shrub is high yielding, resistant to beating down, tomentose and stem sun-burn intensified by autumn. Leaves are medium light green, 3–5 lobed. The flower is pentagonal, medium sized, without an anthocyan spot. Raw fibres are white, flesh-coloured or have sandy tints, and are kept firm in the boll without falling out and are suitable for hand and machine picking.

Fibre yield is 34–36% and length 36/38 mm.

By the end of vegetation growth, the self-defoliation reaches 100 per cent. The plant has a tendency to drying in the apical or top section, leading to some "self-embossing" of plants.

The white and coloured fibres are unaffected by sunlight.

The fibre is ecologically favourable, i.e. it does not contain toxins on its surface, and the variety has 95–100% early natural self defoliation.

The invention has been described in detail for the purposes of clarity and understanding of the invention. Various forms and embodiments may be made by a person skilled in the art without departing from the scope of the invention.

References cited herein are listed on the following pages, and are incorporated herein by this reference.

REFERENCES

1. Kim S C et al (1997) Nucleic acids Research 25: 1085–1086.
2. Brian H et al (1994) Methods in Plant Molecular Biology and Biotechnology. pp. 37–47.
3. Scott O et al (1994) Plant Molecular Biology Manual D1: 1–8.

---

---

What is claimed is:

1. A method for producing a self-defoliating cotton plant, comprising: (A) selfing a first cotton plant or crossing it with a second cotton plant, such that progeny seeds are produced, wherein said first cotton plant is of variety "Rainbow 39," represented by a deposit under AGAL Accession No. NM 98/06259; (B) harvesting and growing said progeny seeds under conditions for plant growth, whereby progeny plants are produced; and (C) selecting among said progeny plants to obtain at least one progeny plant with a self-defoliating phenotype.

2. An F1 generation, self-defoliating cotton plant produced by the method of claim 1.

3. A cotton plant or a part thereof, wherein said cotton plant is of variety "Rainbow 39", and is grown from seed, representative seed deposited under AGAL Accession No. NM 98/06259.

4. Seed produced by selfing the cotton plant according to claim 3, wherein said seed produce a self-defoliating cotton plant.

5. A self-defoliating cotton plant produced by the process comprising (A) selfing a cotton plant such that progeny seeds are produced, wherein said cotton plant is of variety "Rainbow 39" represented by a deposit under AGAL accession No. NM 98/06259; (B) harvesting and growing said progeny seed under conditions for plant growth, whereby progeny plants are produced; and (C) selecting among said progeny plants to obtain at least one progeny plant with a self-defoliating phenotype.

6. Seed produced by selfing the cotton plant according to claim 5, wherein said seed produce a self-defoliating cotton plant.

7. The seed of claim 6, being of said variety "Rainbow 39".

8. A part of the cotton plant of claim 5.

\* \* \* \* \*

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 1
ctcagtcgca                                                                10

<210> SEQ ID NO 2
<211> LENGTH: 227
<212> TYPE: DNA
<213> ORGANISM: Gossypium hirsutum

<400> SEQUENCE: 2
gtctaaaatg caggaggacc agaactaact caacgccact caacactata cctcggatcc        60
cacaggagcc ctggcttgtc cctctgtgct cactcatcct ttcccgtgtc gttaactaat       120
gtctgcctac aggagggagt tgttgcagtc aagggaaatg atccctaaaa ttctctacgc       180
tgcaccattc cccgatcaag accatgtgat tcatgaaaat tataaca                    227
```